United States Patent [19]
Lee et al.

[11] Patent Number: 5,569,746
[45] Date of Patent: Oct. 29, 1996

[54] PROCESS FOR PREPARING ALKYLSUBSTITUTED CYCLOPENTADIENYL METALLOCENE COMPOUNDS

[75] Inventors: John Y. Lee; Edward A. Burt, both of Baton Rouge, La.

[73] Assignee: Albemarle Corporation, Richmond, Va.

[21] Appl. No.: 376,973

[22] Filed: Jan. 23, 1995

[51] Int. Cl.$^6$ .............................. C07F 5/00; C07F 17/00; C07F 7/00
[52] U.S. Cl. ..................... 534/11; 556/43; 556/52; 556/53; 556/58; 556/70; 556/87; 556/136; 556/140; 556/143
[58] Field of Search ................... 556/53, 43, 52, 556/58, 70, 87, 136, 140, 143; 534/11

[56] References Cited

U.S. PATENT DOCUMENTS 4,874,880  10/1989  Miya et al. ............................ 556/53
5,200,537  4/1993   Lee et al. ............................. 556/11
5,302,733  4/1994   Diefenbach et al. ..................... 556/11
5,359,105  10/1994  Strickler et al. ...................... 556/410

FOREIGN PATENT DOCUMENTS 0582480  2/1994  European Pat. Off. .

Primary Examiner—Porfirio Nazario-Gonzales
Attorney, Agent, or Firm—David M. Bunnell

[57] ABSTRACT

A process for making a metallocene, said process comprising the steps of (a) reacting an alkylsubstituted cyclopentadiene ligand, which contains a mixture of endo- and exo-isomers, with up to about a 10% excess over a stoichiometric amount of a deprotonation agent based on the amount of endo-isomers, so as to form a salt of said endo-isomers, (b) reacting the endo-isomer salt with a transition or actinide metal compound so as to form said metallocene and (c) optionally separating said exo-isomers and trace amounts of unreacted endo-isomers from said metallocene by distillation.

8 Claims, No Drawings

PROCESS FOR PREPARING ALKYLSUBSTITUTED CYCLOPENTADIENYL METALLOCENE COMPOUNDS

This invention relates generally to the preparation of metallocene compounds and more specifically to a process for preparing metallocenes of improved purity from alkylcyclopentadiene ligands which are mixtures of endo- and exo-isomers.

Metallocenes of the formula $ML_x$, where M is a transition or actinide metal, L represents ligands co-ordinated with the metal atom, at least one of the ligands having a cyclopentadienyl skeleton, and x is the oxidation number of the metal, are known in the art to be useful in forming catalysts for olefin polymerization.

The metallocenes can be prepared by deprotonating a cyclopentadienyl containing ligand with a deprotonating agent such as an alkali metal, an alkali metal alkyl, or a Grignard reagent and then reacting the resulting ligand salt with the transition or actinide metal compound. Usually about a stoichiometric to about a 10% excess of deprotonating agent is used based on the total amount of ligand. It has been found that when the ligand is substituted with at least two groups which are individually alkyl or together form a cycloalkyl ring, such that the ligand contains both endo- and exo-isomers, then the metallocene product can contain significant amounts of by-product impurities, including the exo-isomers which remain unreacted. Furthermore, attempts to purify the product using an acid wash will cause the exo-isomers to oligomerize and the oligomer must then be removed from the product which requires additional purification steps. We have now discovered a process which results in the direct production of metallocene products of high purity without expensive purification procedures.

In accordance with this invention there is provided a process for making a metallocene, said process comprising the steps of (a) reacting an alkylsubstituted cyclopentadiene ligand, which contains a mixture of endo- and exo-isomers, with up to about a 10% excess over a stoichiometric amount of a deprotonation agent based on the amount of endo-isomers, so as to form a salt of said endoisomers, (b) reacting the endo-isomer salt with a transition or actinide metal compound so as to form said metallocene and (c) optionally separating said exo-isomers from said metallocene by distillation.

Also provided is a metallocene which contains a ligand which comprises a polyalkylsubstituted cyclopentadienyl skeleton, which metallocene is substantially free of exo-isomers of polyalkylsubstituted cyclopentadienes and oligomers thereof.

As indicated above, the process of the invention is useful in making metallocenes by deprotonating a ligand which contains a cyclopentadienyl moiety in which the cyclopentadienyl ring is substituted in a manner such that it contains a mixture of endo- and exo-isomers and then reacting the deprotonated ligand with a transition or actinide metal compound. Such metallocenes can be represented by the formula $ML_x$, where M is a transition or actinide metal, L represents ligands coordinated with the metal atom, at least one of the ligands having a polyalkyl substituted cyclopentadienyl skeleton, and x is the oxidation number of the metal. Examples of the ligands which are mixtures of endo- and exo-isomers are those in which the cyclopentadiene ring is substituted with at least two alkyl or substituted alkyl groups, where two adjacent groups can be joined to form a $C_4$–$C_6$ ring and where the groups contain from 1 to about 30 carbon atoms. Non-limiting examples of such groups include methyl, ethyl, n-propyl, isopropyl, n-butyl, isobutyl, tert-butyl, amyl, isoamyl, hexyl, cyclohexyl, heptyl, octyl, nonyl, 1,2-dimethylene, 1,2-trimethylene, 1,2-tetramethylene, and the like.

Non-limiting examples of transition and actinide metals include Ti, Zr, Hf, V, Cr, Th, U, and the like. Preferred for catalyst use are the Group IVB metals Ti, Zr and Hf.

Examples of specific metallocenes which can be made by the process of the invention include:

Bis(4,5,6,7-tetrahydroindenyl)zirconium dichloride,

Ethylenebis(4,5,6,7-tetrahydroindenyl)zirconium dichloride,

Dimethylsilylenebis(dimethylcyclopentadienyl)zirconium dichloride,

Dimethylsilylenebis(trimethylcyclopentadienyl)zirconium dichloride,

Dimethylsilylenebis(4,5,6,7-tetrahydroindenyl)zirconium dichloride,

Bis(dimethylcyclopentadienyl)zirconium ethoxychloride,

Bis(dimethylcyclopentadienyl)zirconium bis(trifluoromethanesulfonate),

Bis(methylethylcyclopentadienyl)zirconium chloride,

Bis(methylpropylcyclopentadienyl)zirconium dichloride,

Bis(methylbutylcyclopentadienyl)zirconium dichloride,

Bis(methylbutylcyclopentadienyl)zirconium bis-(methanesulfonate),

Bis(trimethylcyclopentadienyl)zirconium dichloride,

Bis(tetramethylcyclopentadienyl)zirconium dichloride,

Bis(pentamethylcyclopentadienyl)zirconium dichloride.

In the compounds exemplified above, the di-substituted cyclopentadienyl ring includes 1,2- and 1,3-substituted compounds, and the tri-substituted cyclopentadienyl ring includes 1,2,3- and 1,2,4-substituted compounds. Further, the alkyl groups such as propyl or butyl include isomers such as n-, i-, sec-, and tert-alkyl groups.

Similar specific compounds include the above named compounds in which Zr is replaced by Ti, Hf, V, Cr, U and Th.

An example of a typical ligand which is a mixture of endo- and exo-isomers is 1-methyl-3-n-propyl-cyclopentadiene.

In theory there are 5 possible stable endo-isomers and 3 possible stable exo-isomers. The structure of one isomer of each type is illustrated below:

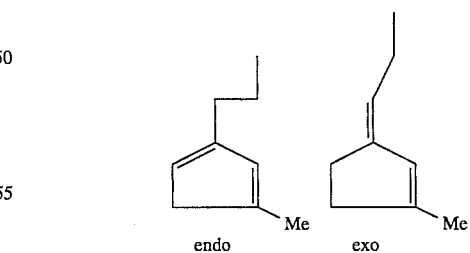

endo    exo

A suitable procedure of the preparation of di-alkylsubstituted cyclopentadiene ligands is described, for example, in copending allowed application Ser. No. 08/137,683, whose teachings are incorporated herein by reference. The process gives improved yields of the endo-isomers, but the product still contains 25 to 30 percent of the exo-isomers.

In accordance with the invention we have found that by selecting the amount of deprotonation agent to be used based on only the amount of endo-isomers which are present, the amount of by-product impurities is reduced such that a highly pure metallocene product can be produced. Likewise, the amount of metal salt used for the metallization reaction is also preferably based on the endo-isomer content such that remaining unreacted metal salt in the product is minimized. At the same time, the exo-isomer remains stable under these reaction parameters and can be easily removed from the product by vacuum distillation. In contrast, when the stoichiometry is chosen based on the total amount of both endo- and exo-isomers in accordance with the prior art, the product is impure and requires expensive work-up procedures to remove the impurities. If the reagents were pure, then only stoichiometric amounts could be used, based on the amount of endo-isomers. However, because of impurities and/or moisture, as a practical matter, up to about a 10 percent excess over the stoichiometric amounts of deprotonating agent and metal compound based on the amount of endo-isomers, is preferably used. This gives a good yield of product while still minimizing the amount of by-product impurities. For example, in forming an unbridged bis-cyclopentadienyl metallocene, about 1.1 mole of deprotonating agent and about 0.55 mol of metal compound per mol of endo-isomer are preferably used.

Suitable deprotonating agents include, for example, Na powder, RLi, NaH, LiH or a Grignard reagent (RMgX, where R is $C_1$ to $C_{10}$ hydrocarbyl and X is halogen). Preferred are alkyllithium compounds such as methyllithium, n-butyllithium, s-butyllithium, t-butyllithium, phenyllithium, and the like.

Suitable reaction solvents are aliphatic or aromatic hydrocarbon or halohydrocarbon solvents and ethers, including mixtures of these solvents. For example the deprotonating agent, contained in a hydrocarbon solvent such as hexanes, cyclohexane, heptane, pentane, toluene and the like is added to an acyclic or cyclic ether solution of the ligand. Alternatively, the deprotonating agent in hexanes or a mixture of hexanes and toluene can be added to the dry ligand, with diethyl ether or THF being added, if necessary, to provide a thinner, more workable solution. Reaction temperatures can range from about −20° to 120° C. and preferably from about 0° to 60° C.

The ligand salt from the deprotonation reaction is reacted with a transition or actinide metal compound and, preferably a metal halide, in order to form the metallocene. The metal compound is preferably used in the form of its ether or THF complex; although it can be used directly as a metal halide. The ligand salt need not be recovered from the deprotonation reaction mixture prior to the metallization reaction and can be added to the metal compound or vise versa. The reaction solvents and temperatures can be the same as for the deprotonation reaction. At higher temperatures, a closed system is conveniently used to avoid the loss of solvent and, especially, ether. The by-product metal halide salts which precipitate can be either removed by filtration or the product solution decanted off. The solvents can be removed, for example, at ≦40° C. and 70–80 mm Hg and the exo-isomer distilled off, for example, at ≦10 mm Hg and ≦80° C. The yield of crude product is >95% based on endoisomers and the purity >95% with <5% ligand oligomer such that the product metallocene can be used in catalyst manufacture without any purification other than the above stripping of solvent and exo-isomers. The distillation of exo-isomers will also remove any trace amounts of unreacted endo-isomers.

The invention is further illustrated by, but is not intended to be limited to, the following examples.

EXAMPLE 1

Freshly distilled and dried (over $MgSO_4$) 1-n-butyl-3-methylcyclopentadiene ligand (6.80 g, 50 mmol, containing 38.5 mmol of endo-isomers and 10 mmol of exo-isomers, remainder impurities) and $Et_2O$ (20.4 g) were charged under nitrogen into a 100-mL, 3-necked, round-bottom flask equipped with a thermometer, magnetic stirring bar, and an addition funnel. BuLi (2.5 M in hexanes, 16.0 ml, 40 mmol) was added at 22° to 35° C. over a period of 60 minutes (to react with the endo-isomers and impurities to form a very thick Li ligand salt solution ($Et_2O$ is added to keep it workable if needed). The mixture was stirred overnight and checked by $^1H$ NMR. A 10% excess (based on endo-isomers) of BuLi was then added to balance the stoichiometry. The mixture was stirred for additional 4 hours and $^1H$ NMR indicated a >95% conversion of endo-isomers. The exo-isomers were found stable under these reaction conditions. $ZrCl_4$ (18 mmol, 4.19 g) was added at 22° to 35° C. slowly over a period of 30 minutes. The product mixture was stirred overnight, checked by $^1H$ NMR, and then up to 2 mmol of $ZrCl_4$ were added to balance the stoichiometry. This product mixture was stirred overnight. The $^1H$ NMR indicated a complete conversion of Li ligand salt. The exo-isomers were found stable under these reaction conditions. The dark orange/red solution of bis(1-n-butyl-3-methyl-cyclopentadienyl)$ZrCl_2$ product was decanted. The wet cake was rinsed and decanted twice with $Et_2O$ to give a total of 66.14 g of solution. $^1H$ NMR (with $CH_2Br_2$ as internal standard) indicated a 97.4% yield of product. $Et_2O$ and hexanes were removed at ≦40° C. and 70–80 mm Hg to give 9.55 g of oily residue which solidified at 22° C. Exo-isomers were distilled off at ≦1 mm Hg and ≦80° C. to give 8.17 g of crude product which solidified at 22° C. $^1H$ NMR indicated that the crude product was >95% pure (<5% oligomer was detected). The yield is >95% based on endo-isomers. The purity of the distilled exo-isomers is up to 97% pure by CG and $^1H$ NMR. Zr wt %=20.9 (21.06 in theory) and Cl wt %=17.1 (16.4 in theory); Li level=234 ppm.

EXAMPLE 2

Freshly distilled and dried (via azeotropic toluene strip) 1-n-butyl-3-methylcyclopentadiene (14.53 g, 52.3 weight percent in toluene, 71.6% endo-isomers, 40.0 mmol exo-isomers, 15.9 mmol) and $Et_2O$ (22.8 g) were charged under nitrogen into a 100 mL, 3-necked, round-bottom flask equipped with a thermometer, magnetic stirring bar, and an addition funnel. BuLi (2.5M in hexanes, 16.0 ml, 40.0 mmol) was added at 22° to 35° C. over a period of 30 minutes to form a thick Li solution. This mixture was stirred overnight. $^1H$ NMR indicated a >90% conversion of endo-isomers. Additional BuLi (2.5 mol) was added to give >95% conversion of endo-isomers. The exo-isomers were found to be stable under these reaction conditions. Toluene (10.0 g) and $ZrCl_4$ (4.95 g, 21.25 mmol) were stirred under nitrogen in a 100-mL flask. $Et_2O$ (3.7 g, 50 mmol) was slowly added into above slurry at 22° to 30° C. to form $ZrCl_4 \cdot 2Et_2O$. The Li ligand salt solution was slowly added into the $ZrCl_4 \cdot 2Et_2O$ solution over a period of 30 minutes at 22° to 30° C. to form an orange product mixture and by-product LiCl solids. The $^1H$ NMR of a 5-hour sample (with $CH_2Br_2$ as internal standard) indicated a complete conversion of Li ligand salt and a >90% yield of product. The exoisomers and a trace of unreacted endo-isomers were found to be stable under these reaction conditions.

The exo-isomers and non-reacted endo-isomers can be removed by distillation as described in Example 1. Also, any hydrolyzed product (oxo compound) can be converted back to the product by a HCl wash. Because the exo-isomers have previously been removed by distillation, the problem of oligomer formation due to the acid wash is eliminated.

What is claimed is:

1. A process for making a metallocene, said process comprising the steps of (a) reacting an alkylsubstituted cyclopentadiene ligand, which contains a mixture of endo and exo isomers, with up to about a 10% excess over a stoichiometric amount of a deprotonation agent, based on the amount of endo-isomers, so as to form a salt of said endo-isomers, (b) reacting the endo-isomer salt with a transition or actinide metal compound so as to form said metallocene and (c) optionally separating said exo-isomer from said metallocene by distillation.

2. The process according to claim 1 wherein said exo-isomers are separated from said metallocene by distillation.

3. The process according to claim 1 wherein said endo-isomer salt is reacted with up to about a 10% excess over a stoichiometric amount of transition or actinide metal salt.

4. The process according to claim 3 wherein said exo-isomers are separated from said metallocene by distillation.

5. The process according to claim 1 wherein said alkyl-substituted cyclopentadiene is a 1,2-dialkylsubstituted cyclopentadiene.

6. The process according to claim 1 wherein said alkyl-substituted cyclopentadiene is a 1,3-dialkylsubstituted cyclopentadiene.

7. The process according to claim 1 wherein said transition or actinide metal compound is a halide of said transition or actinide metal.

8. The process according to claim 1 wherein said metallocene has the formula $ML_x$, where M is a transition or actinide metal, L represents ligands coordinated with the metal, at least one of the ligands having cyclo-pentadienyl skeleton which is substituted with at least two alkyl groups which may be joined to form a $C_4$–$C_6$ ring, and x is the oxidation number of the metal.

* * * * *